United States Patent [19]

Jacobson

[11] 4,337,271
[45] Jun. 29, 1982

[54] ERYTHRO-9,10-DIHYDROXYOCTADECAN-1-OL ACETATE A BOLL WEEVIL ANTI-FEEDANT

[75] Inventor: Martin Jacobson, Silver Spring, Md.

[73] Assignee: The United States of America as represented by the Secretary of Agriculture, Washington, D.C.

[21] Appl. No.: 229,215

[22] Filed: Jan. 28, 1981

[51] Int. Cl.³ ............................................. A01N 37/02
[52] U.S. Cl. ..................................................... 424/311
[58] Field of Search ..................... 424/311; 252/363.5, 252/364; 560/263

[56] References Cited

U.S. PATENT DOCUMENTS 2,627,489  2/1953  Drake ................................. 560/263

OTHER PUBLICATIONS

D. D. Hardee and T. B. Danich, *J. of Economic Entomology*, vol. 59, No. 5, 1966 pp. 1267–1270, (PTO Chem. Lib.).

Jacobson et al.; Talk Presented at National Meeting of The Entomological Society of America, Denver, Colorado, Nov. 25–29, 1979.

*Primary Examiner*—Albert T. Meyers
*Assistant Examiner*—F. T. Moezie
*Attorney, Agent, or Firm*—M. Howard Silverstein; William E. Scott; David G. McConnell

[57] ABSTRACT

Erythro-9,10-Dihydroxyoctadecan-1-ol acetate, a compound isolated in low yield from tung oil, was synthesized in high yield and found to have excellent potential as a boll weevil feeding deterrent when applied to cotton plants.

3 Claims, No Drawings

ERYTHRO-9,10-DIHYDROXYOCTADECAN-1-OL ACETATE A BOLL WEEVIL ANTI-FEEDANT

BACKGROUND OF THE INVENTION

1. Field of the Invention

This invention relates to a feeding deterrent for the boll weevil, Anthonomus grandis Boheman, to a method of deterring the boll weevil from feeding and to a method of preparing a boll weevil feeding deterrent.

2. Description of the Art

The presence in tung oil of an unidentified feeding deterrent for the boll weevil was reported in J. Econ. Entomology 59, 1267–1270, 1966. The use of methyl α-eleostearate as a boll weevil feeding deterrent and a method for obtaining α-eleostearic acid from tung oil are described in patent application Ser. No. 140,911, filed Apr. 16, 1980.

SUMMARY OF THE INVENTION

It is an object of this invention to provide an effective boll weevil feeding deterrent as an alternative or supplement to the use of insecticides to control boll weevils in the growing of cotton.

It is a further object of the invention to provide a method of treating cotton with a boll weevil feeding deterrent.

In general, according to this invention the above objects are accomplished by applying to growing cotton plants an effective boll weevil deterrent amount of erythro-9,10-dihydroxyoctadecan-1-ol acetate which is synthesized by the method described later in this specification.

DESCRIPTION OF THE INVENTION

Since tung oil was known to contain an unidentified feeding deterrent for the boll weevil I investigated and successfully isolated from it two compounds, namely α-eleostearic acid and erythro-9,10-dihydroxyoctadecan-1-ol acetate. The use of the former compound and its isolation from tung oil are described in the previously noted patent application Ser. No. 140,911, filed Apr. 16, 1980.

Erythro-9,10-dihydroxyoctadecan-1-ol acetate, which has not been described previously, is a very stable compound and is a strong boll weevil feeding deterrent. However, it is present in tung oil only to the extent of 0.02%. Therefore, I devised a method of synthesizing the compound.

In accordance with the invention, growing cotton plants are treated with the deterrent by application in any suitable way such as by spraying or by dusting. It is preferred to apply the agent by spraying and more preferably by means of aqueous spray from conventional commercial spraying equipment. The effect of the application of erythro-9,10-dihydroxyoctadecan-1-ol acetate on growing cotton is illustrated as follows:

A one percent (1%), wgt/vol, solution in a suitable solvent (acetone) of the feeding deterrent is applied to an unpunctured, debracted bud of a greenhouse-grown cotton plant by momentarily dipping the bud into the solution. Ten one or two day old adult boll weevils, unfed from time of emergence or starved for 24 hours, are placed in a petri dish with one treated bud and one control bud that is first dipped in the same solvent (acetone) only and held for four hours. The number of feeding punctures per bud is counted under a dissecting microscope. The bud treated with erythro-9,10-dihydroxyoctadecan-1-ol acetate sustained only 9 punctures, whereas the control bud sustained 68 punctures. Acetone was used as the solvent in this example. However, other solvents in which the compound is soluble and which are preferably inert, may be used.

Erythro-9,10-dihydroxyoctadecan-1-ol acetate is an odorless, white crystalline solid melting at 54°, insoluble in water but readily soluble in ethyl ether, acetone, methanol, and ethanol. On the basis of its structure, it probably has no toxicity or very low toxicity to mammals, birds, fish, and insects.

Erythro-9,10-dihydroxyoctadecan-1-ol acetate (I) is prepared by the following process:

Oleic acid (II) is reduced in 97% yield to oleyl alcohol (Z-9-octadecen-1-ol) (III) by treatment with lithium aluminum hydride. Although compound III is available commercially, it is available only in a purity of about 85%; the impurities present in the commercial product are extremely difficult to separate from compound I obtained later. Compound III dissolved in benzene is caused to react at low temperature with acetyl chloride to yield 85% of oleyl acetate (Z-9-octadecen-1-ol acetate) (IV). Compound IV was hydroxylated to compound I in 40% yield by treatment with hydrogen peroxide in tert-butanol in the presence of a catalytic amount of osmium tetroxide, according to the method described in J. Org. Chem. 28, 320, 1963, for the cis hydroxylation of olefins.

The following examples further exemplify the preparation of erythro-9,10-dihydroxyoctadecan-1-ol acetate (I).

EXAMPLE 1

(Z)-9-Octadecen-1-ol (III)

A solution of compound II (12 g) in 50 ml of dry ether was slowly dripped into a stirred suspension of 2 g of lithium aluminum hydride in 100 ml of dry ether. Gentle refluxing was maintained during addition, and the mixture was then refluxed for an additional 30 minutes. The mixture was chilled in an ice bath and treated gradually with 35 ml of ice water followed by 50 ml of cold 10% $H_2SO_4$. The ether layer was separated, the aqueous layer was shaken with two portions of ether, and the combined ether layers were dried over anhydrous $Na_2SO_4$. Evaporation of the solvent and distillation of the residue gave 11.1 g (97%) of compound III which boiled at 150° (0.02 mm), $n_D^{25}$ 1.4608.

EXAMPLE 2

(Z)-9-Octadecen-1-ol acetate (IV)

a solution of 2.8 g of acetyl chloride in 10 ml of dry benzene was added dropwise, with stirring, to an ice-cold solution of compound III (5.0 g) and 2.8 g of pyridine in 20 ml of dry benzene. Following addition, stirring was maintained at room temperature for 30 minutes and the mixture was then refluxed for 2 hours. The cooled mixture was diluted with 30 ml of ether and treated with sufficient cold 5% HCl to make the mixture strongly acid. The layers were separated and the aqueous layer was shaken once with 20 ml of ether; the combined organic layers were washed with three 10-ml portions of cold $H_2O$ and dried over $Na_2SO_4$. Evaporation of the solvent and distillation of the residue gave 5.1 g (85%) of compound IV as a colorless liquid boiling at 139°–143° (0.1 mm), $n_D^{25}$ 1.4493.

EXAMPLE 3

Erythro-9,10-Dihydroxyoctadecan-1-ol acetate (I)

Osmium tetroxide ($OsO_4$) catalyst solution was prepared by dissolving 1 g of $OsO_4$ in 122 ml of tert-butanol (purified by distillation over solid $KMnO_4$) and adding 30% $H_2O_2$ dropwise until the color remained pale green. Compound IV (2.0 g) was dissolved in a mixture of 16 ml of acetone and 4 ml of ether and this solution was treated with a mixture of 2 ml of catalyst solution and 2 ml of 30% $H_2O_2$. The brown solution was stirred at 30° for 24 hours, then cooled to 15° and the ether and acetone were distilled off at 15 mm pressure. The solid that separated was filtered off and recrystallized once from dilute ethanol to give 860 mg (40%) of compound I as colorless crystals melting at 54°.

Infrared spectrum: There are strong absorption peaks at 3299 (OH), 1740 (primary ester), 1100–1300 (secondary OH), and 1240 $cm^{-1}$ (acetate).

Analysis—Calcd. for $C_{20}H_{40}O_4$ (percent): C, 70.00; H, 11.63. Found (percent): C, 69.91; H, 11.64.

I claim:

1. A method of deterring boll weevils from feeding in growing cotton plants comprising applying to said plants an effective boll weevil deterrent amount of erythro-9,10-dihydroxyoctadecan-1-ol acetate.

2. The method of claim 1 wherein the erythro-9,10-dihydroxyoctadecan-1-ol acetate is applied by spraying.

3. The method of claim 1 wherein the erythro-9,10-dihydroxyoctadecan-1-ol acetate is applied as an aqueous spray.

* * * * *